United States Patent [19]

Bergstresser et al.

[11] Patent Number: 5,447,500
[45] Date of Patent: Sep. 5, 1995

[54] COLLAR AND CARTRIDGE-NEEDLE UNIT ASSEMBLY

[75] Inventors: William A. Bergstresser, Prattsburgh; Mark A. Stiehl, Rochester, both of N.Y.; John J. Niedospial, Princeton Junction, N.J.

[73] Assignee: Sterling Winthrop, Inc., Malvern, Pa.

[21] Appl. No.: 129,932

[22] Filed: Sep. 29, 1993

[51] Int. Cl.⁶ .............................................. A61M 5/32
[52] U.S. Cl. ................................... 604/198; 604/197; 604/263
[58] Field of Search ............................ 604/240-243, 604/198, 200, 201, 204, 919, 192, 187, 110, 197, 263; 285/921, 902

[56] References Cited

U.S. PATENT DOCUMENTS

| | | | |
|---|---|---|---|
| 2,828,743 | 4/1958 | Ashkenaz et al. | 604/201 |
| 4,288,112 | 9/1981 | Stoll | 285/921 |
| 4,568,336 | 2/1986 | Cooper | 604/201 |
| 4,585,445 | 8/1985 | Hadtke . | |
| 4,720,285 | 1/1988 | Pickhard | 604/240 |
| 5,033,513 | 7/1991 | Bartholomew | 285/921 |
| 5,141,500 | 8/1992 | Hake | 604/198 |
| 5,312,370 | 5/1994 | Talonn et al. | 604/198 |
| 5,314,414 | 5/1994 | Hake et al. | 604/197 |

FOREIGN PATENT DOCUMENTS

| | | |
|---|---|---|
| 485028 | 5/1992 | European Pat. Off. . |
| PCT/US91/-06878 | 2/1993 | WIPO . |
| PCT/US91/-05613 | 4/1993 | WIPO . |

*Primary Examiner*—C. Fred Rosenbaum
*Assistant Examiner*—Mark Bockelman
*Attorney, Agent, or Firm*—William J. Davis

[57] ABSTRACT

This invention relates to a collar adapted for use in combination with activatable prefilled cartridge-need units and disposable holders. The collar is adapted to fit over the hub of the cartridge-needle unit and comprises a solid circumferential neck; a circumferential foot interrupted in at least one point having inside and outside arcuate surfaces, the outside surface having thereon a circumferentially outwardly extending ring and the inside surface having thereon at least one radially inwardly extending shelf; and at least one leg connecting the neck to the foot. The collar provides improved safety reliability and thus reduces the susceptibility of health care workers to accidents, e.g., accidental needle strikes. In addition, the collar can be easily and economically manufactured, e.g., by conventional precision injection molding techniques.

4 Claims, 6 Drawing Sheets

COLLAR AND CARTRIDGE-NEEDLE UNIT ASSEMBLY

BACKGROUND OF THE INVENTION

1. Field of the Invention

This invention relates to a collar adapted for use with pre-filled cartridge-needle units and disposable holders to form a syringe assembly.

2. Description of the Prior Art

Disposable medicament-containing cartridge needle units for use in conjunction with reusable hypodermic syringe holders are well known in the art and in widespread commercial use. Such cartridges conventionally feature a cylindrical body closed at the proximal end with a flexible plunger slidable within the bore of the cartridge and closed at the distal necked-down end with a septum secured to the cartridge by a crimped-on aluminum collar. The necked-down distal end conventionally is fitted with a needle hub/needle/sheath assembly. Such cartridge-needle units are available from Sanofi Winthrop Pharmaceuticals under the Carpuject® trademark.

In use, the cartridge-needle unit must be activated, i.e., the proximal end of the needle cannula must penetrate the sealed septum such that communication is achieved between the fluid and the proximal end of the needle. Some cartridge-needle units are sold in an activated form. Others must be activated by the user. When user activated cartridge-needle units are used in conjunction with conventional reusable syringe holders of the type described, for example, in Hadtke, U.S. Pat. No. 4,585,445 and in EP-A 485,028, this is accomplished when the health care worker advances the cartridge through the holder by rotating a clamping element.

Many holders, including the above-referenced reusable holders, enable the user to avoid handling the cartridge-needle unit when the needle unit is exposed. Nevertheless, health care workers are especially susceptible to accidental and potentially infectious, and indeed, on occasion, possibly fatal, needle strikes due to the careless handling and/or disposing of the cartridge-needle unit after use. The consequences to health care workers of strikes from needles contaminated with various infectious diseases such as hepatitis or AIDS can be particularly severe. The frequency of such accidental needle strikes in the United States is surprisingly great, and has been estimated to be approximately one million strikes per year. Moreover, the cost to health care organizations for the testing of health care workers accidentally stricken by used needles is a significant burden on health care costs. Therefore, it would be desirable to further protect health care workers by providing systems which reduce the possibility of accidental needle strikes.

To this end, it has been suggested to provide a hollow body to house the cartridge-needle unit, such that the needle can be exposed for use and then withdrawn into the body for safety. For example, PCT/US91/06878 describes disposable, i.e., single use, holders which can be used in conjunction with cartridge-needle units. This system features a holder containing a radially deformable body having an elliptical cross-section; and an adapter having a circumferentially extending adapter ring sized to engage specifically positioned pairs of body slots formed in the body. However, in practice, the adapter designs proposed in PCT/US91/06878 function less than satisfactorily and result in unacceptable safety and reliability risks during use. For example, the prior art adapters do not adequately retain the needle hub. This can lead to failures when the cartridge-needle unit is thrust forward by the user during activation and delivery, or during retraction. Further, the proposed prior art adapter designs significantly increase the force required to activate the cartridge-needle unit, which can lead to failure of the syringe assembly to function for its intended purpose. Additionally, it is virtually impossible to manufacture the prior art adapters in a manner that would enable the syringe assemblies to be sold at a price which would enable them to be competitive in significant segments of the market. Consequently, these systems are less than fully satisfactory from a commercial standpoint.

In addition, existing safety syringe systems often are not economical to manufacture and/or assemble in large quantities. This is especially true when the syringe system is intended to be disposable.

It would be desirable to provide an improved collar for use with a cartridge-needle unit and holder which enables the system to be assembled and used safely and easily and which reduces the susceptibility of health care workers to accidental needle strikes.

SUMMARY OF THE INVENTION

We have discovered an improved collar for use in combination with a cartridge-needle unit and disposable holders, which collar is easy to use and manufacture and which reduces the susceptibility of health care workers to accidental needle strikes.

More specifically, in accordance with this invention, there is provided a collar adapted to fit over the hub of a cartridge-needle unit comprising a solid circumferential neck; a circumferential foot interrupted in at least one point and having inside and outside arcuate surfaces, the outside surface having thereon a circumferentially outwardly extending ring and the inside surface having thereon at least one radially inwardly extending shelf; and at least one leg connecting the neck to the foot.

It is an advantageous feature of this invention that a collar is provided for use in combination with cartridge-needle units and disposable holders which improves the safety and reliability of the syringe system and reduces the susceptibility of health care workers to accidental needle strikes.

It is another advantageous feature of this invention that a collar is provided which exhibits improved needle-hub retention capabilities and which can be easily and economically manufactured by conventional precision injection molding techniques.

Still another advantageous feature of this invention is that a one-piece collar is provided which reduces the tendency of the cartridge-needle units to be activated prematurely during assembly.

Other advantages will become readily apparent upon reference to the following description of preferred embodiments when read in light of the accompanying drawings.

DESCRIPTION OF PREFERRED EMBODIMENTS

In a preferred embodiment, the collar of this invention is used in conjunction with a pre-filled cartridge-needle unit and a hub/needle/sheath subassembly. As depicted in FIGS. 1–4, collar 9 comprises at the distal end thereof a circumferential neck 11 which is a solid annular ring defining an opening which is designed to fit over the safety needle sheath of a cartridge-needle unit hub/needle/sheath subassembly. The proximal end of the collar comprises a circumferential foot 13. The foot is interrupted in at least one, and preferably, in two places on opposite sides of the foot. The interruptions provide a degree of flexibility which enables the collar to readily snap over the hub. The foot can be interrupted in more than two locations. The combination of the solid ring and interruptions, i.e., slots in the foot, enable the collar to be assembled into the cartridge-needle unit with minimal risk of premature cartridge activation. The interruptions permit the collar to be assembled on the cartridge-needle unit with a low assembly force (high assembly force can lead to premature activation during the assembly process). Moreover, this combination provides excellent resistance to forward thrusts made during activation and drug delivery.

Each foot portion has an inside arcuate surface 15 and an outside arcuate surface 17. The outside surface of the foot has thereon a circumferentially outwardly extending ring 19. Such ring is sized to be accepted in a holder having a body comprising specially positioned slots as described further hereinbelow. The inside surface of the foot has thereon at least one radially inwardly extending retention shelf 21. The shelf preferably extends inwardly from the inside surface of the foot at an angle of about 90°. The purpose of the shelf is to trap the skirt of the hub inside the collar by engaging the proximal end of the skirt of the hub, i.e., the hub seats on the surface of the shelf. A shelf angle of about 90° with respect to the longitudinal axis of the collar is particularly preferred. Applicants have found that this angle enables the collar to provide maximum retention capability of the hub within the collar.

In a preferred embodiment, the collar of this invention is provided with at least one pair of ribs 23 extending longitudinally from the neck to the foot. The ribs prevent inadvertent removal of the cartridge-needle unit and prevent readvancement of a retracted needle.

The collar of this invention comprises at least one leg 25 connecting the neck to the foot. Two or more legs can be present. In a particularly preferred embodiment, six legs are present. The legs in conjunction with the neck and foot define one or more windows. Applicants have discovered that at least one window must be present in order to prepare the above-described collar having a 90° shelf by conventional injection molding techniques. The presence of at least one window and 90° shelf enable improved manufacturability and excellent hub retention capabilities.

The collar of this invention provides many significant advantages over prior art adapter designs. For example, the solid neck provides several advantages compared to adapters proposed in the prior art without closed necks. Applicants have discovered that the prior art adapters without closed necks do not adequately retain the cartridge-needle unit when the cartridge-needle unit is thrust forward, e.g., during activation of the unit and/or during delivery of the contents of the unit. Consequently, cartridge-needle units can be thrust out of the prior art adapters, resulting in a potentially dangerous loss of control over the needle. Additionally, the prior art adapters can on occasion be retracted completely through and out of the body of the holder. This, of course, is undesirable, inasmuch as a potentially contaminated needle is exposed. Further, the prior art adapter designs significantly increase the force required to activate the cartridge, whereas the collar of this invention does not. Increased activation force can lead to lack of activation, which renders the cartridge-needle unit useless.

Figure 1:
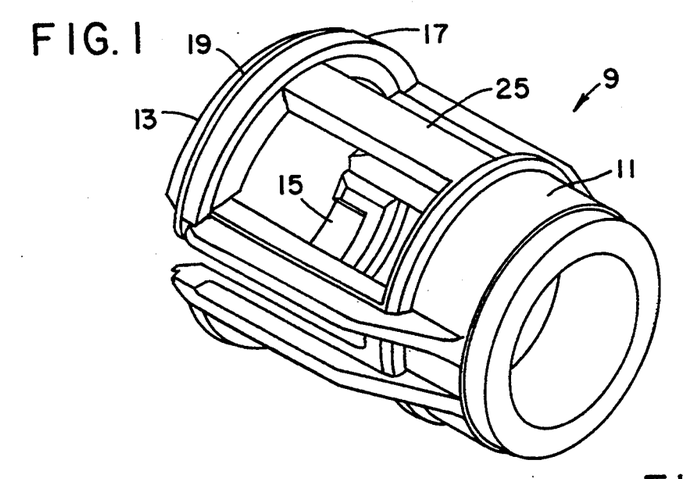
FIG. 1 is a perspective view of a preferred embodiment of a collar in accordance with this invention.
Figure 2:
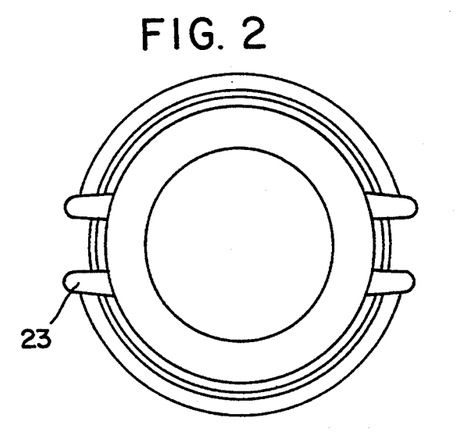
FIGS. 2–4 are top and cross-sectional front and side views of the collar depicted in FIG. 1.
Figure 3:
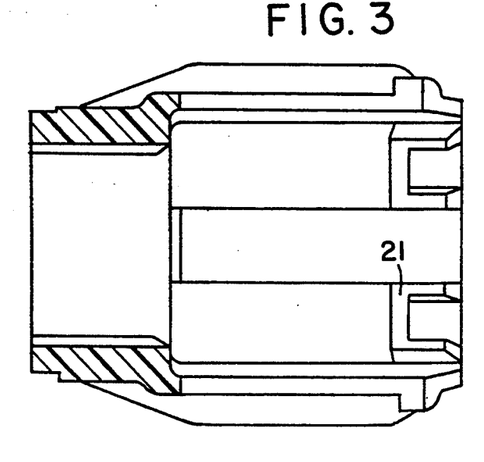
Figure 4:
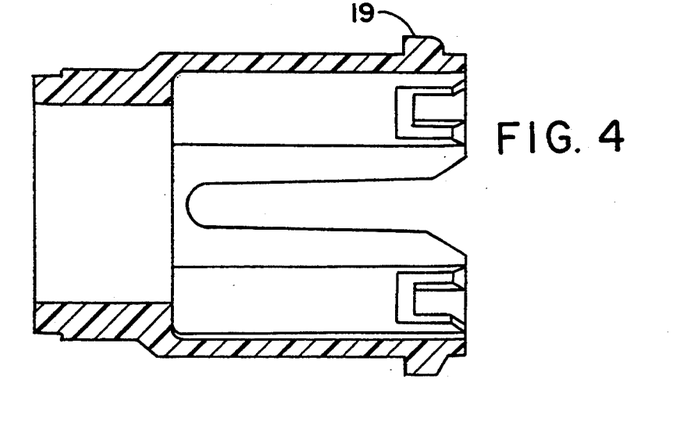
Figure 5:
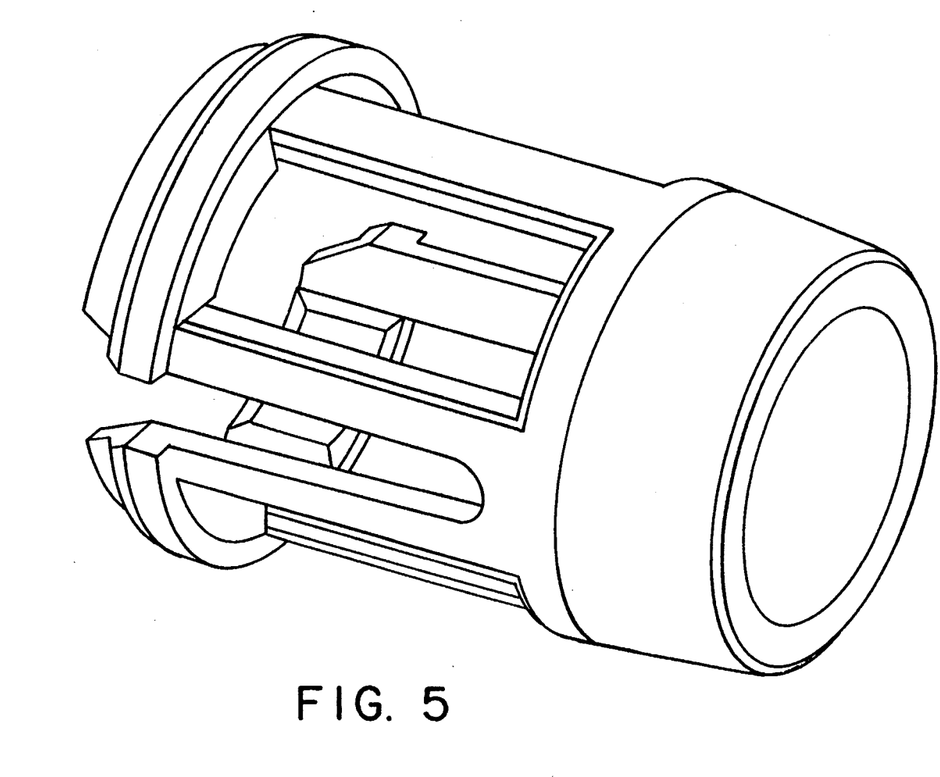
FIG. 5 is a perspective view of another embodiment of this invention.
Figure 6:
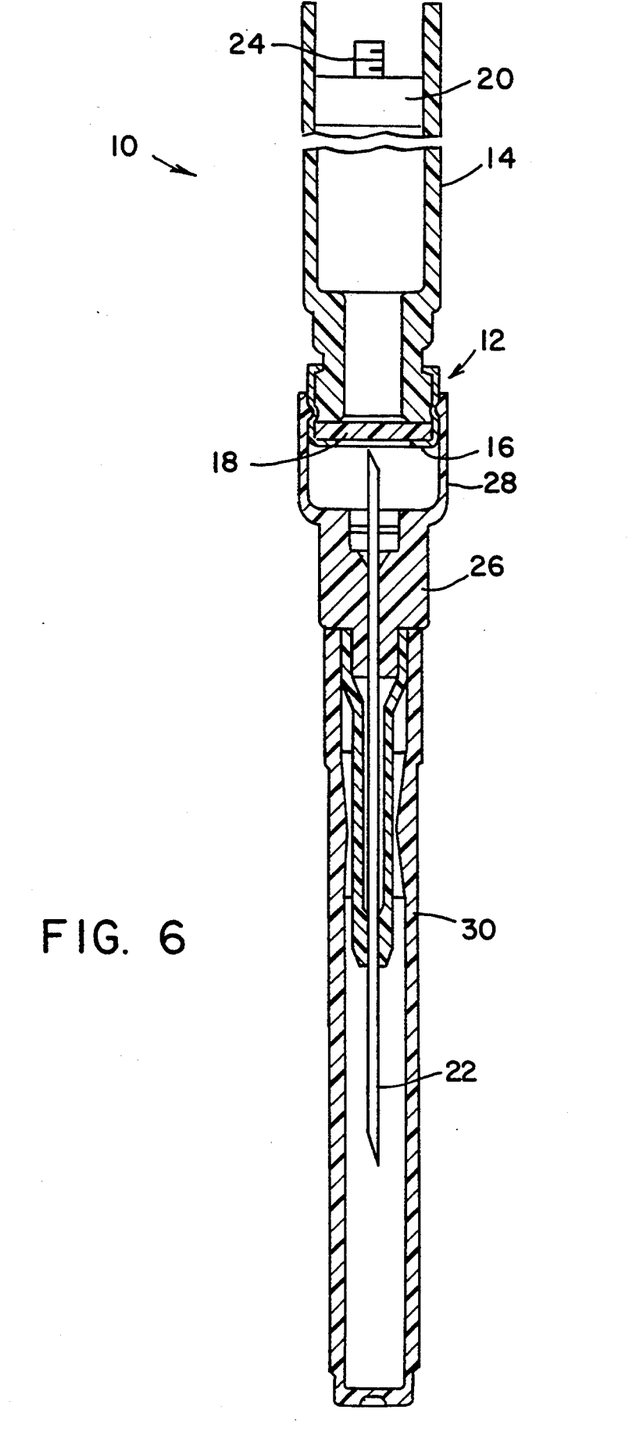
FIG. 6 illustrates a cartridge-needle unit hub/needle/sheath subassembly useful in combination with the collar of this invention.
Figure 7:
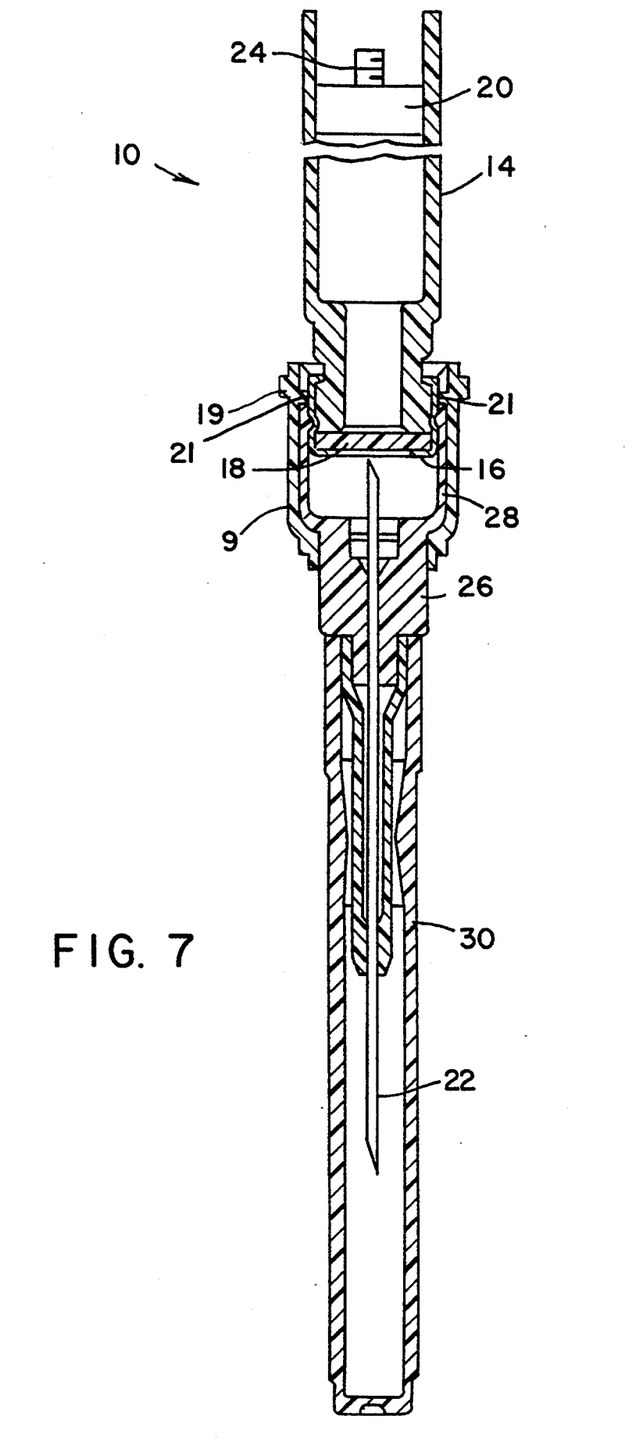
FIG. 7 illustrates the collar of this invention engaged with the cartridge-needle unit hub/needle/sheath subassembly having the skirt of the hub inside the collar.

The prefilled cartridge-needle unit can be of a conventional design and can include a hollow, transparent body, typically fabricated of glass, which is prefilled with a supply of fluid medication or the like. Such cartridge-needle units currently are in widespread commercial use. With reference to FIG. 6, the cartridge 10 includes head portion 12 and a cylindrical body 14 which are coextensively joined together at a relatively narrow neck. A metallic end cap 16 covers a sealed septum 18 which extends across the distal end of the cartridge to prevent contamination and leakage of the fluid contents. Plunger 20 is sized to be received in and slidable axially and reciprocally through the interior of the cartridge. The plunger is formed from a relatively dense resilient material, e.g., rubber, and can be moved distally through the cartridge for expulsing the fluid contents of the cartridge via needle cannula 22 so as to project outwardly from the end thereof. Screw-threaded post 24 can be mated to a screw-threadable plunger rod of an associated holder to complete a plunger assembly for controlling the movement of the plunger through the interior of the cartridge. The plunger rod can comprise a plurality of ribs extending longitudinally on the interior surface of the cavity adapted to be threaded onto the post. An advantage of this design is that the plunger can be manufactured by conventional injection molding techniques. It is contemplated that other means known in the art can be employed for attaching the rod to the plunger stem.

The necked-down distal end of the cartridge-needle unit can be fitted with a hub/needle/sheath subassembly. Hub 26 can be attached to the cartridge by snapping skirt 28 over the distal end of the cartridge to engage the metallic end cap. Needle-sheath 30 covers the needle prior to use.

Figure 8:
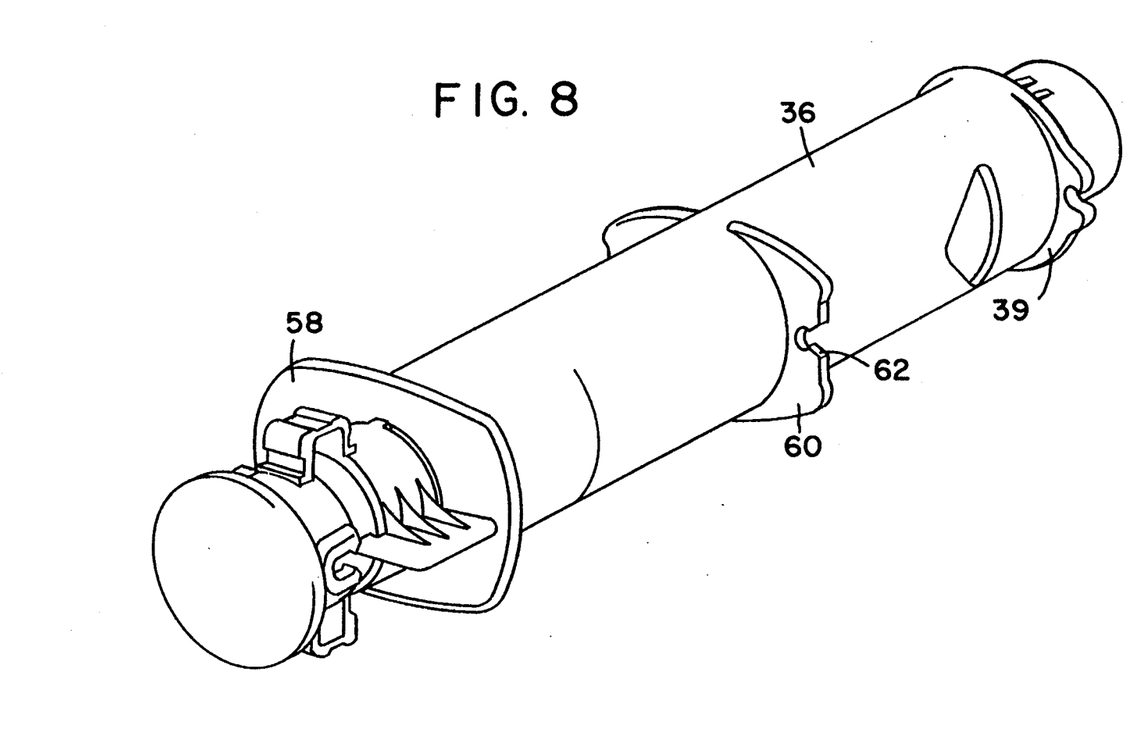
FIG. 8 illustrates a preferred holder for use with the collar of this invention.

The collar of this invention can be used in conjunction with any holder featuring slots sized to accept the ring on the foot of the collar. For example, the collar can be used with the holder described in PCT/US91/06878. In a preferred embodiment, the collar can be used in conjunction with a holder, such as depicted in FIG. 8, comprising a hollow body 36 and sized for housing the cartridge-needle unit therein, and means for permitting the body to move axially relative to the cartridge-needle unit. In one preferred embodiment, the holder comprises a hollow body having a substantially elliptical cross-section at the distal end and a substantially circular cross-section at the proximal end. The elliptical distal end preferably can be squeezably deformable. The circular cross-section preferably is sized to surround the cartridge-needle unit Such a holder featuring a so called "transition body" i.e., a body which has an elliptical cross-section at the distal end, a circular cross-section at the proximal end, and a smooth transition therebetween provides additional advantages. For example, cartridge-needle units tend to be unstable in a holder featuring a body which is solely elliptical in cross-section, because they are inadequately supported. The instability of such systems, in practice, can lead to unacceptable safety risks. Further, elliptically shaped bodies require alignment during assembly. On the other hand, the circular cross-section at the proximal end of the above-described holder facilitates alignment of the cartridge-needle unit both during assembly of the syringe system and during use. Moreover, the circular cross-section can be sized such that it does not permit the cartridge-needle unit to be pulled through the proximal end of the holder during retraction, thus avoiding a risk to the user's safety. The circular shaped body can effectively block the circumferential ring from further axial movement in the proximal direction. Finally, a body having a circular shaped proximal end facilitates use of a cap intended to be threaded onto the proximal end of the body.

Figure 9:
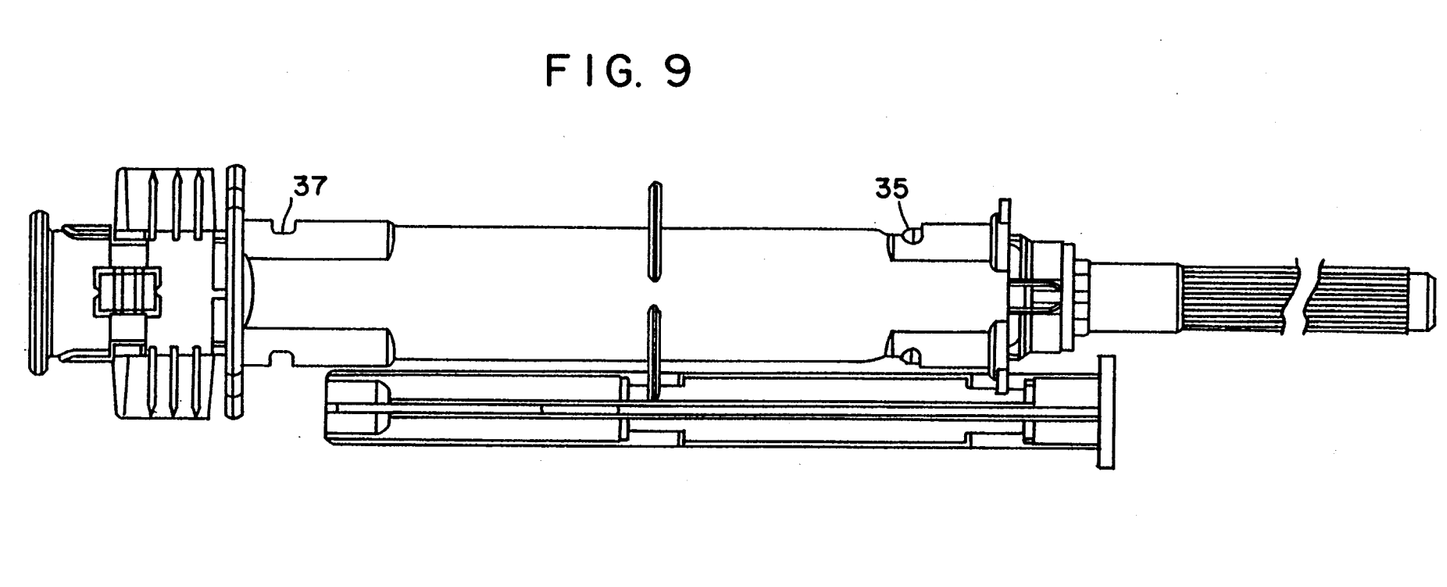
FIG. 9 illustrates a collar, cartridge-needle unit hub/needle/sheath holder assembly in accordance with this invention.

The body can comprise one or more retaining slots 35 (FIG. 9) at the distal end thereof and one or more retaining slots 37 at the proximal end thereof. The slots are sized to accept the circumferential ring of the collar. The outer circumference of the ring can enter the retaining slots when the body is in its normal undeformed condition. To disengage the adapter ring from the retaining slots, the user squeezes the body opposite the retaining slots, i.e., inwardly along the major axis of the ellipse, thereby permitting the body to move axially with respect to the cartridge-needle unit. The retaining slots are preferably positioned so that the cartridge-needle unit is held in place in a use position and in a safe position, i.e., such that the tip of the needle cannula is within the interior of the body.

In another preferred embodiment, the body comprises a pair of cam slots 39 (FIG. 8) disposed within the distal end of the body. In a preferred embodiment, the cam slots are triangular in shape. It is a particular advantage that cam slots are self activating and do not require user interface. In other words, cam slots do not require that the user squeeze the body in order to release the ring from the slots. This is a particular advantage both from the standpoint of ease of use and user safety. When cam slots are present, health care workers are not required to squeeze the body to free the ring to permit the body to move. In addition to the safety advantage of not requiring one hand of the user to be near the used needle, the free hand can be used in conjunction with retraction finger guards 60 to facilitate the retraction of the cartridge-needle unit into the body of the holder.

In a preferred embodiment of this invention, the proximal end of the cartridge-needle unit is provided with a cap. The cartridge-needle unit, if activatable, preferably can be activated by application of force to the cap. The force can be applied to the cap directly, e.g., by twisting the cap, and/or indirectly, e.g., through a lever element.

In a preferred embodiment, the holder is provided with finger flange 58 to facilitate the injection process. When the holder comprises cam slots, it is particularly preferred that retraction finger guards 60 be provided to facilitate retraction of the cartridge-needle unit into the holder in a safe and reliable manner. The body can be provided with retention feature 62 which permits the plunger rod to be attached via a snap fit to the holder.

The collar of this invention can be fabricated of any suitable material including metals and plastics. However, it is well adapted to be made of plastic. In particular, the collar and associated holder can be fabricated of rigid plastic using known precision injection molding techniques. Suitable plastics include polypropylene, polystyrene, polycarbonates, ABS (clear or opaque), nylon, acetals, polyethylene or polyester. The material can include a slip agent or lubricant to facilitate the sliding motion of the body with respect to the collar. A preferred slip agent is PETRAC SLIP-EZE OLEAMIDE, a fatty amide commercially available from Synpro, Cleveland, Ohio.

In use, the collar of this invention operates in conjunction with a holder and conventional cartridge-needle units needle/hub/sheath assemblies for administration of an injection as follows. First, the plunger rod can be unsnapped from the body of the syringe assembly. If necessary, the cartridge-needle unit can be activated, e.g., by applying force to the cap. The cap is then removed, for example, by grasping the twist tabs and applying a sharp twisting motion, to expose the plunger. The associated plunger rod can then be attached to the exposed plunger, e.g., by threading it onto the post and turning clockwise. Next, the sheath is removed to expose the needle cannula. The needle is inserted into an injection site and an axially and distally directed force is applied by the health care worker to the plunger rod via the thumb pad. The distal force is transferred from plunger rod to plunger, to drive the plunger through medicament-containing cartridge-needle unit and to thereby expulse the fluid contents of the cartridge via the needle cannula into the injection site. After the injection is administered, the needle cannula is removed from the injection site. Subsequently, the body can be grasped behind the retraction finger guards, and the cartridge-needle unit can be pulled proximally back by the user such that the ring is accepted and locked into place by the distal retaining slots and the exposed needle is withdrawn into and held within the body of the holder, thus significantly reducing the possibility of accidental needle strikes. The holder-used cartridge-needle unit combination can be disposed of in an appropriate manner.

The invention has been described in detail with particular reference to certain preferred embodiments thereof, but it will be understood that variations and modifications can be effected within the spirit and scope of the invention.

What is claimed is:

1. A collar, cartridge-needle unit, holder assembly comprising in combination,
   (1) a collar adapted to fit over the hub of an activatable cartridge-needle unit, said collar comprising:
      a solid circumferential neck:
      a circumferential foot interrupted in at least one point, said foot having inside and outside arcuate surfaces, said outside surface having thereon a circumferentially outwardly extending ring and said inside surface having thereon at least one radially inwardly extending shelf, wherein said shelf extends inwardly from the inside surface of the foot at an angle of about 90°; and at least two legs connecting said neck to said foot, said outwardly extending ring extending between said legs;

(2) an activatable cartridge-needle unit comprising a hub having a skirt having a proximal end, said collar being fitted over the hub such that the shelf is engaged with the proximal end of the skirt; and (3) a holder having a hollow body housing said cartridge-needle unit therein, said body comprising slots engaged with said outwardly extending ring on the foot of said collar.

2. The collar cartridge-needle unit, holder assembly of claim 1 wherein said circumferential foot is interrupted in two points.

3. The collar cartridge-needle unit, holder assembly of claim 1 wherein said collar comprises six legs.

4. The collar cartridge-needle unit, holder assembly of claim 1 wherein said collar further comprises two pairs of ribs extending longitudinally from said neck to said foot.

* * * * *